US00PP14828P3

(12) United States Plant Patent
Hasegawa

(10) Patent No.: US PP14,828 P3
(45) Date of Patent: May 25, 2004

(54) HYBRID CARNATION PLANT NAMED 'CFPC MINDY'

(50) Latin Name: *Dianthus caryophyllus*
Varietal Denomination: CFPC Mindy

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,171

(22) Filed: Jul. 29, 2002

(65) Prior Publication Data

US 2004/0019943 P1 Jan. 29, 2004

(51) Int. Cl.[7] ..... A01H 5/00
(52) U.S. Cl. ..... Plt./276
(58) Field of Search ..... Plt./276

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive light lavender flowers.

1 Drawing Sheet

Classification: The present invention relates to a new Hybrid *Dianthus caryophyllus* plant.

Variety denomination: The new plant has the varietal denomination 'CFPC Mindy'.

BACKGROUND OF THE INVENTION

The present invention relates to a new and distinct variety of carnation plant which was discovered by me as a naturally occurring sport in a controlled planting of 'CFPC Passion' (U.S. Plant Pat. No. 10,416). The varietal denomination of the new variety is 'CFPC Mindy'.

SUMMARY OF THE INVENTION

Among the novel characteristics possessed by the new variety which distinguish it from other varieties of which I am aware, are its attractive light lavender flowers which retain color without fading. When grown in a greenhouse in Salinas, Calif., in 4½ inch plastic pots, pinched plants are about 9 inches tall and about 7 inches in diameter. Flower diameter averages about 2 inches with a crown of about ¾ inch (average). Foliage is about 3½ inches long and about 5/16 inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENTS

The new variety differs from its parent in flower color.

BRIEF DESCRIPTION OF ILLUSTRATION

The accompanying illustration shows a typical specimen of the vegetative growth and flowers of the new variety depicted in color as nearly true as it is reasonably possible to make the same in color illustration of this character.

DESCRIPTION OF THE NEW VARIETY

The following is a detailed description of the new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, type, suitable for cut flower production and as a pot spray.

Plant:
- *Height.*—About 9 inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Very vigorous and free-breaking plant habit with strong straight stems.
- *Mutation prone.*—No.
- *Disease resistance.*—Good, resistence to soil-borne diseases such as *Fusarium oxysporum,* and *F. graminearum* and root-rots such as damping off, water molds and the like as is typical of carnations.
- *Temperature tolerance.*—Wide range.

Foliage (base of plant):
- *Color.*—Upper side: Near 137A. Lower side: Near 137B.
- *Size.*—About 3½ inches long and about 5/16 inch wide.
- *Leaf base and apex.*—Leaf base edge smooth, color near 138D; leaf apex edge smooth, color near 137A.
- *Quantity.*—Numerous.
- *Shape.*—Lanceolate.

*Texture.*—Smooth.
*Ribs.*—Central keel.
*Arrangement.*—Bi-lateral along stem.
*Stem.*—Color: Near 137A at maturity. Size: Stem diameter about 1/8 inch.
*Bud.*—Shape: Ovoid. Color.: Near 143C. Length: About 1 1/8 inches. Diameter: About 3/8 inch.
*Calyx.*—Sepals: About 5. Length: About 5/16 inch. Width: About 1/4 inch. Color Outside: Near 144C. Inside: Near 145D.

Bloom:
*Shape.*—Rounded.
*Size.*—Diameter: About 2 inches. Depth: About 3/4 inch.
*Borne.*—As a spray.
*Color.*—General tonality: Red-purple. Upper side: Near 65C. Lower side: Near 65D. Center: Near 65C. Outer petals: Near 65C.
*Permanence.*—Dry up on receptacle.
*Keeping quality.*—Very good, 3+ weeks.
*Fragrance.*—Slight.

Petalage:
*Quantity.*—About 21.
*Outer petal size.*—Length: About 1 7/8 inches. Width: About 1 1/8 inches.
*Central petal size.*—Length: About 1 13/16 inches. Width: About 1 inch.
*Texture.*—Smooth.
*Appearance.*—Shiny, petal edge very finely serrated, color near 65C.
*Form.*—Fan shaped.

Reproductive organs:
*Stamen.*—None.
*Anthers.*—None.
*Filaments.*—None.
*Pistil.*—1. Length: About 1 1/4 inches. Color: Whiter than 155D.
*Stigma.*—2 (bi-lobed). Color: Near 65D.
*Fertility.*—Male: Sterile. Female: Good.
*Ovary.*—Shape: Conical. Color Base: Near 155D. Body: Near 144B. Apex: Near 144B.
*Fruit.*—No fruit or seed produced.

I claim:

1. A new and distinct carnation plant of the variety substantially as herein shown and described.

* * * * *

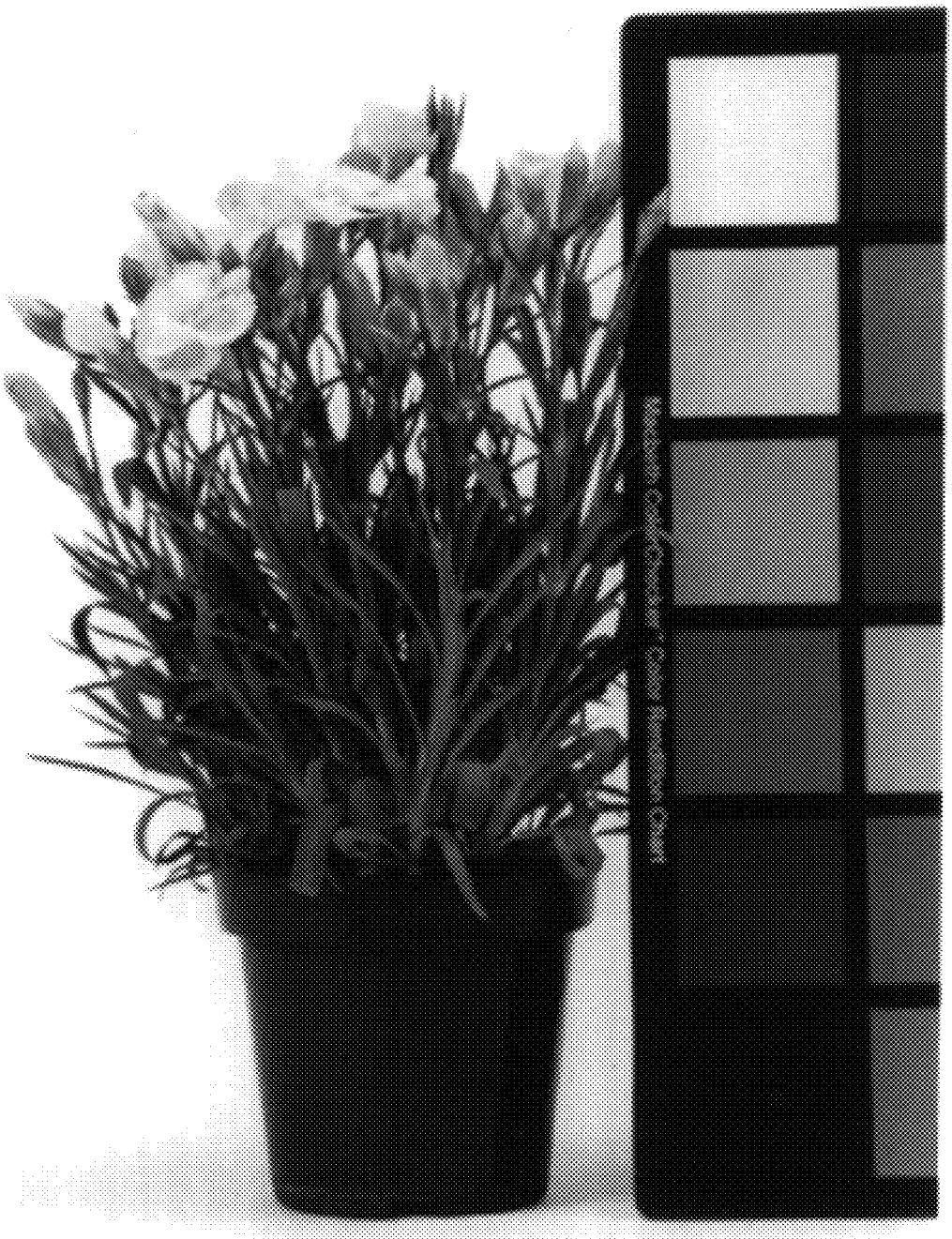
Kimberly Queen Fern